United States Patent [19]

Madsen et al.

[11] 4,357,343

[45] Nov. 2, 1982

[54] NUTRITIONAL COMPOSITION FOR MANAGEMENT OF RENAL FAILURE

[75] Inventors: David C. Madsen, Libertyville; Hugh N. Tucker, Chicago, both of Ill.

[73] Assignee: Baxter Travenol Laboratories, Inc., Deerfield, Ill.

[21] Appl. No.: 277,526

[22] Filed: Jun. 26, 1981

[51] Int. Cl.³ .................... A61U 31/40; A61U 31/195
[52] U.S. Cl. ...................................... 424/274; 424/319
[58] Field of Search ................................ 424/274, 319

[56] References Cited

PUBLICATIONS

Physicians' Desk Reference, 31st Ed., 1977, p. 1566.

Primary Examiner—Stanley J. Friedman
Attorney, Agent, or Firm—Max D. Hensley; Lawrence W. Flynn; Paul C. Flattery

[57] ABSTRACT

A novel amino acid composition is provided for the nutritional maintenance of renal failure patients.

11 Claims, No Drawings

NUTRITIONAL COMPOSITION FOR MANAGEMENT OF RENAL FAILURE

BACKGROUND OF THE INVENTION

This invention relates to compositions and methods for nutritional management of renal failure. In particular it is directed at novel amino acid compositions for meeting the specialized nutritional requirements of patients suffering renal failure and the attendant derangements of normal amino acid metabolism and dialysis-induced losses in the body's amino acid complement.

Renal failure may be classified as acute or chronic. Acute renal failure is characterized by an abrupt, often reversible impairment (partial or total) of renal function, manifested by inadequate urine formation. Acute renal failure usually appears rapidly—on the order of one to several days—either with or without prior renal dysfunction. Urine output may range from total anuria through stages of oliguria, to polyuria in the diuretic (recovery) phase.

Acute renal failure follows from a diversity of possible causes, which are divided into two categories: nephrotoxic injury and renal ischemia. Nephrotoxic injury results from sensitivity response or excessive and/or continuous exposure to drugs, chemicals, heavy metals, etc., which prove toxic to the renal tubular cells, while renal ischemia results from clinical situations causing hypovolemia, hypotension, and/or acute dehydration. Some commonly encountered etiologic factors include: complications of anesthesia, major surgery, obstetrical complications and trauma.

Patients with acute renal failure very often are subject to such complications as sepsis and hypercatabolism. The resulting secondary malnutrition and wasting has resulted in considerable attention being given to nutritional adjuncts to therapy. Previous principles called for severe or total restriction of protein intake to reduce uremia (azotemia). However, more recent therapy has combined very careful protein dosing (including the use of crystalline amino acids) to adequately nourish the patients, with prophylactic dialysis to control uremia.

In contrast with acute renal failure, chronic renal failure is characterized by a gradual destruction of the number of functional nephrons and thus gradual reduction of renal functional capacity. Given the initial reserve renal functional capacity, the kidney can adapt quite well as the disease progresses. Electrolyte balance is often well regulated, but nitrogenous substances (urea, creatinine) accumulate. Chronic renal failure may result from renal circulatory insufficiency, loss of effective renal mass, intrinisic functional disorders, and urinary tract obstruction.

Conservative management, including nutritional therapy, can be successful in prolonging the time before dialysis therapy is initiated. Patients with chronic renal failure are also often malnourished and wasted from anorexia, associated illnesses, unpalatable dietary regimens, uremic "toxins", altered nutrient needs, and the effects of dialysis. Restriction of protein over the long-term is commonly-accepted therapy, but it is difficult to enforce and dangerous, since it can promote chronic tissue wasting.

Instead of, or in conjunction with limiting protein intake the art has attempted to support renal failure patients by supplying amino acids alone in controlled amounts and proportions or as dietary supplements.

It is known to supply amino acids by parenteral or enteral routes for nutrition in renal failure, and to use mixtures of the eight essential amino acids alone (L-leucine, L-phenylalanine, L-methionine, L-lysine, L-isoleucine, L-valine, L-threonine, and L-tryptophan) or supplemented with various nonessential amino acids, many of which have been shown to be effectively essential in the circumstances of renal failure, e.g., histidine. Examples of such amino acid compositions are disclosed in U.S. Pat. No. 3,764,703, West German Offlegungsschriften Nos. 25 31 204, 25 30 246 and 26 33 948, Bergstrom et al., "Clin. Sci Mol. Med." 51: 589–99 (1976); Bergstrom et al., "Clin. Sci. Mol. Med." 54: 51–60 (1978); Furst et al., "Am. J. Clin. Nutr." 31: 1744–55 (1980); Motil et al., "JPEN" 4: 3235 (1980) and Piraino et al., Second Congress of the European Society of Parenteral and Enteral Nutrition. Newcastle Upon Tyne, September 1980.

None of the heretofore employed amino acid mixtures are considered by applicants to be of optimal benefit in nutritional support during renal failure, particularly concomitant with dialysis. A formulation has been needed which will produce the most favorable clinical response as measured by plasma and intracellular amino acid profiles approaching normal, protein turnover and nitrogen balance.

Accordingly it is an object of this invention to supply an amino acid composition which will contribute to the attainment of positive nitrogen balance.

It is another object to normalize both the intracellular and plasma amino acid concentrations in renal failure patients, including such patients undergoing frequent dialysis.

These and other objects of the invention will be apparent from the specification as a whole.

SUMMARY OF THE INVENTION

The objects of the invention are realized by carefully selecting the relative proportions of amino acids to be employed in nutritional maintenance of renal failure patients. The compositions of this invention are defined by the following amino acids in the approximate recited mole percent ranges.

| Amino Acid | Mole Percent Range |
| --- | --- |
| L-Leucine | 8.6 to 8.9 |
| L-Phenylalanine | 5.6 to 5.8 |
| L-Methionine | 7.2 to 6.5 |
| L-Lysine (free base) | 5.8 to 6.0 |
| L-Isoleucine | 7.2 to 7.5 |
| L-Valine | 12.1 to 13.6 |
| L-Histidine | 5.2 to 6.9 |
| L-Threonine | 5.9 to 6.3 |
| L-Tryptophan | 1.4 to 1.5 |
| L-Alanine | 11.7 to 12.4 |
| Glycine | 7.7 to 8.9 |
| L-Arginine | 5.6 to 7.0 |
| L-Proline | 5.9 to 6.2 |
| L-Tyrosine | 0.3 to 0.6 |
| L-Serine | 5.5 to 6.3 |

This composition is suitable for parenteral or enteral administration. Administration by the parenteral mode entails infusing the composition as a sterile aqueous solution at a concentration of about from 3 to 15 grams of amino acids/dl. Ordinarily, it is infused at a rate of about from 2 to 10 grams of nitrogen per day, although the precise dosage will depend upon the clinical circumstances.

Enteral, or oral administration is generally accompanied by ingestion of other required nutrients such as minerals, vitamins and assimilable calories, all of which may be combined with the amino acid composition of the invention before administration or supplied through ordinary dietary sources.

DETAILED DESCRIPTION OF THE INVENTION

The ranges of amino acid proportions recited above, the concentrations of administered solutions, and the rate of administrating may be varied to refine the responsiveness of the renal failure patient in the particular clinical circumstances at hand, e.g., progress and extent of renal failure, presence of complications or other diseases states such as diabetes, and whether or not dialysis is concurrent. These factors and the degree of dietary protein restriction, if any, are balanced to arrive at optimal maintenance.

The effectiveness of the dietary program may be monitored by well known assays for assessing renal function in dialyzed or non-dialyzed patients as appropriate. Suitable examples include serum urea nitrogen (SUN), SUN/creatinine ratio, urea nitrogen appearance and glomerular filtration rate for creatinine. Other diagnostic mechanisms will be apparent to the ordinary artisan.

The relative proportions of amino acids are preferably within 5% of the ranges recited above, although each range may be varied by as much as 15%. Nonetheless, the proportion of essential amino acids to the nonessential amino acids by weight should be at least about 1.5 to 1.

The concentration of amino acids in a sterile solution for parenteral infusion or injection will vary depending primarily upon the clinical desirability of the infused or injected water. Generally, it is not desirable to infuse highly dilute solutions, i.e., less than about 2% by weight, because such water must then be removed through the patient's weakened kidneys or by dialysis. Concentrated solutions, however, may be osmotically intolerable depending upon the infusion site. Generally, a maximum concentration of about 10% by weight is employed in peripheral venous administration, although solutions of up to about 15% by weight may be infused satisfactorily by central venous catheter.

The solids concentration in enteral solutions containing amino acids, carbohydrates and fats is expressed in terms of osmolarity at a given kcal dosage. At 1.35 kcal/ml, the osmolarity will range about from 350 to 550 mOsm/l, although about 470 mOsm/l is preferred. The amino acid concentration is not critical and will range about from 1 to 10 g/dl.

The parenteral solution is preferably administered by central venous catheter at a daily rate of about from 2.0-5.0 grams of nitrogen or about from 13-32.5 grams of amino acids. This amount of amino acids will be infused in a volume of about from 500 to 1500 ml. Preferably the amino acid solution is combined before or at the time of infusion with a solution of an available carbohydrate such as dextrose or oligosaccharide and a fat emulsion. Such carbohydrate and fat sources are well known and commercially available. A typical formulation is made by combining 250 ml of a solution containing 6.5 per dl of amino acids in the above proportions with 500 ml of 70% dextrose, thereby yielding a solution available for infusion which comprises about 2.2% amino acids and 44% dextrose. This solution has a calorie nitrogen ratio of 276:1. Other such preparations will be well within the skill of the ordinary artisan.

The parenteral and enteral vehicles for the improved amino acid composition herein are preferably essentially free of electrolytes. The parenteral formulation may contain a small amount, e.g. less than 50 mEq/l anions such as chloride but will be essentially free of cations, especially sodium and potassium.

Organic acids such as malic, tartaric and acetic acid, may be supplied to the enteral and parenteral formulations for purposes of pH adjustment and oxidation control. The solution for infusion should be adjusted within the range of about from 6.0 to 7.0, although the pH of the enteral product need not be as closely controlled.

The invention will be more fully understood by reference to the following examples.

EXAMPLE 1

This example demonstrates the formulation and use of the enteral feeding composition of this invention.

The dry formulation contained the following amounts of nutrients per 112 g packet:

|  | Quantity (g) |
| --- | --- |
| Essential Amino Acids | 0.74 |
| L-Leucine | 0.62 |
| L-Isoleucine | 0.92 |
| L-Valine | 0.55 |
| L-Lysine Acetate (free base) | 0.70 |
| L-Methionine | 0.60 |
| L-Phenylalanine | 0.46 |
| L-Threonine | 0.20 |
| L-Tryptophan |  |
| Nonessential (in healthy subjects) Amino Acids |  |
| L-Histidine | 0.52 |
| L-Arginine | 0.64 |
| L-Proline | 0.46 |
| Glycine | 0.43 |
| L-Alanine | 0.68 |
| L-Serine | 0.43 |
| L-Tyrosine | 0.06 |
| Fats |  |
| Medium-Chain Triglycerides | 4.3 |
| Sunflower Oil | 2.8 |
| Carbohydrates |  |
| Glucose Oligosaccharides, Sucrose | 144.5 |
| Vitamins |  |
| Vitamin A | 0 |
| Vitamin D | 0 |
| Vitamin E | 0 |
| Vitamin C | 15 mg |
| Folic Acid | 16.7 mcg |
| Vitamin $B_1$ | 250 mcg |
| Vitamin $B_2$ | 283 mcg |
| Niacin | 3.33 mg |
| Vitamin $B_6$ | 1.7 mg |
| Biotin | 50 mcg |
| Pantothenic Acid | 0.83 mg |
| Vitamin K | 0 |
| Choline | 41.7 mg |

Lecithin was added as an emulsifying agent. Tartrate and malate were included to reduce the pH of the composition to a point at which maximum solubility of the amino acids was achieved. The amino acids, carbohydrates and fat were responsible for 32, 379 and 56 kcal, respectively, per 112 g lot.

The composition was essentially free of electrolytes and contained only water soluble vitamins.

The composition was dissolved in 270 ml of water to yield 350 ml of a nutrient fluid containing about 1.2 g total nitrogen, about 467 kcal and an osmolarity at standard dilution (1.35 kcal/ml) of 470 mOsm/l.

It was administered slowly by an enteral feeding tube to a 60 year old male acute renal failure patient who had undergone significant weight loss and was unable to sit up and ingest a normal diet. The feeding rate was about 20 grams/hour, but the initial approximate 12 hours of feeding was conducted with a half-strength solution. The patient was fed continuously, during which hemodialysis was conducted regularly. After 5 days the patient was alert and was able to consume solid foods.

EXAMPLE 2

This example is concerned with the formulation and parenteral use of the improved composition disclosed herein.

A sterile, nonpyrogenic hypertonic solution containing the following amino acid concentrations per 100 ml was provided:

|  | mg/100ml |
| --- | --- |
| Essential Amino Acids |  |
| L-Leucine | 600 |
| L-Phenylalanine | 490 |
| L-Methionine | 500 |
| L-Lysine (HCL Salt) | 450 |
| L-Isoleucine | 500 |
| L-Valine | 816 |
| L-Threonine | 380 |
| L-Tryptophan | 160 |
| Nonessential (in healthy subjects) Amino Acids |  |
| L-Alanine | 560 |
| Glycine | 300 |
| L-Histidine | 420 |
| L-Arginine | 630 |
| L-Proline | 350 |
| L-Tyrosine | 40 |
| L-Serine | 300 |

In addition the solution contained 20 mEq acetate and 30 mEq of chloride per liter. The pH was about 6.0 (by adjustment with acetic acid). About 3 mEq/l of sodium bisulfite was included as a stabilizer.

A suitable patient for treatment with the composition of this example would be an end stage renal failure patient having carcinoma of the esophagus who has undergone esophageal resection and cannot take any nutrients enterally until the surgery has healed. This patient would be fed 500 ml/day of the above-described product and 500 ml of 70% dextrose/day by central venous catheter. After 14 days of treatment by this regimen, the parenteral infusion could be discontinued and enteral feeding with the Example 1 composition instituted.

I claim:

1. A composition for treating renal failure or deficiency, comprising an amino acid mixture consisting of the following amino acids in the stated proportions:

| Amino Acid | Mole Percent Range about from |
| --- | --- |
| L-Leucine | 8.6 to 8.9 |
| L-Phenylalanine | 5.6 to 5.8 |
| L-Methionine | 7.2 to 6.5 |
| L-Lysine (free base) | 5.8 to 6.0 |
| L-Isoleucine | 7.2 to 7.5 |
| L-Valine | 12.1 to 13.6 |
| L-Histidine | 5.2 to 6.9 |
| L-Threonine | 5.9 to 6.3 |
| L-Tryptophan | 1.4 to 1.5 |
| L-Alanine | 11.7 to 12.4 |
| Glycine | 7.7 to 8.9 |
| L-Arginine | 5.6 to 7.0 |
| L-Proline | 5.9 to 6.2 |
| L-Tyrosine | 0.3 to 0.6 |
| L-Serine | 5.5 to 6.3 |

2. The composition of claim 1 wherein the mole percentages of L-leucine, L-phenylalanine, L-methionine, L-lysine, L-isoleucine, L-valine, L-histidine, L-threonine, L-tryptophan, L-alanine, glycine L-arginine, L-proline, L-tyrosine, and L-serine are, respectively, about 8.6, about 5.7, about 7.2, about 5.8, about 7.2, about 12.1, about 6.9, about 5.9, about 1.5, about 11.7, about 8.9, about 5.6, about 6.1, about 0.5 and about 6.3.

3. The composition of claim 2 further comprising water soluble vitamins and digestively assimilable carbohydrates and fats.

4. The composition of claim 2 in aqueous solution in a concentration of about from 1 to 10 grams of amino acid/dl.

5. The composition of claim 2 which is essentially free of electrolytes and fat-soluble vitamins.

6. A method for treating a renal failure patient, comprising orally administering the composition of claims 2, 3, 4 or 5 to said patient.

7. The composition of claim 1 wherein the mole percentages of L-leucine, L-phenylalanine, L-methionine, L-lysine, L-isoleucine, L-valine, L-histidine, L-threonine, L-tryptophan, L-alanine, glycine L-arginine, L-proline, L-tyrosine, and L-serine are, respectively, about 8.9, about 5.6, about 7.4, about 6.0, about 7.5, about 12.4, about 5.2, about 6.3, about 1.4, about 12.4, about 7.7, about 7.0, about 6.1, about 0.5 and about 5.5.

8. The composition of claim 7 as a sterile aqueous solution at a concentration of about from 3 to 10 grams of amino acid/dl.

9. The composition of claim 7 which is essentially free of electrolytes.

10. The composition of claim 8 wherein the pH is about 6.0.

11. A method for treating a renal failure patient, comprising parenteral administration of the composition of claim 8, 9 or 10 to said patient.

* * * * *